US012279886B1

(12) United States Patent
Chavez et al.

(10) Patent No.: US 12,279,886 B1
(45) Date of Patent: Apr. 22, 2025

(54) SMART GEAR

(71) Applicant: United Services Automobile Association (USAA), San Antonio, TX (US)

(72) Inventors: Carlos J P Chavez, San Antonio, TX (US); Andrea Marie Richardson, San Antonio, TX (US); Janelle Denice Dziuk, Falls City, TX (US); Oscar Roberto Tijerina, San Antonio, TX (US); Valmore M. Smith, San Antonio, TX (US); Gregory David Hansen, San Antonio, TX (US); Gregory Brian Meyer, San Antonio, TX (US); Courtney St. Martin, Duluth, GA (US)

(73) Assignee: United Services Automobile Association (USAA), San Antonio, TX (US)

( * ) Notice: Subject to any disclaimer, the term of this patent is extended or adjusted under 35 U.S.C. 154(b) by 972 days.

(21) Appl. No.: 17/186,321

(22) Filed: Feb. 26, 2021

Related U.S. Application Data

(60) Provisional application No. 62/983,308, filed on Feb. 28, 2020.

(51) Int. Cl.
| | |
|---|---|
| *A61B 5/00* | (2006.01) |
| *A41D 1/00* | (2018.01) |
| *A61B 5/0205* | (2006.01) |
| *A61B 5/024* | (2006.01) |
| *A61B 5/107* | (2006.01) |
| *A61B 5/145* | (2006.01) |
| *A61F 2/70* | (2006.01) |
| *G06Q 20/32* | (2012.01) |

(Continued)

(52) U.S. Cl.
CPC ........ *A61B 5/6804* (2013.01); *A61B 5/02055* (2013.01); *A61B 5/1077* (2013.01); *A61F 2/70* (2013.01); *G06Q 20/321* (2020.05); *G16H 10/60* (2018.01); *G16H 15/00* (2018.01); *G16H 40/67* (2018.01); *H04Q 9/00* (2013.01); *A41D 1/002* (2013.01); *A61B 5/02438* (2013.01); *A61B 5/14532* (2013.01); *A61B 2560/0214* (2013.01); *A61B 2560/0443* (2013.01); *A61B 2562/028* (2013.01); *A61F 2002/708* (2013.01); *H02J 7/02* (2013.01); *H02J 50/10* (2016.02); *H02J 50/40* (2016.02); *H04Q 2209/40* (2013.01)

(58) Field of Classification Search
None
See application file for complete search history.

(56) References Cited

U.S. PATENT DOCUMENTS

| | | | | |
|---|---|---|---|---|
| 11,223,939 B1 * | 1/2022 | Meyer | ................... | H04W 4/029 |
| 11,497,964 B1 * | 11/2022 | Hunter | ................ | A63B 53/005 |

(Continued)

*Primary Examiner* — Carl H Layno
*Assistant Examiner* — Manolis Pahakis
(74) *Attorney, Agent, or Firm* — Fletcher Yoder, P.C.

(57) ABSTRACT

Smart gear, which includes electrically conductive fabric, is provided to monitor health parameters, conduct transactions, and generate power. For example, the smart gear may include one or more sensors coupled to the fabric and/or electrically conductive fibers woven into the fabric. The one or more sensors may monitor health parameters such as breathing patterns, sleep patterns, heart murmurs, and so forth. The smart gear may include one or more wireless regions that power electronic devices based on inductive charging.

19 Claims, 2 Drawing Sheets

(51) Int. Cl.
  *G16H 10/60* (2018.01)
  *G16H 15/00* (2018.01)
  *G16H 40/67* (2018.01)
  *H02J 7/02* (2016.01)
  *H02J 50/10* (2016.01)
  *H02J 50/40* (2016.01)
  *H04Q 9/00* (2006.01)

(56) References Cited

U.S. PATENT DOCUMENTS

| | | | | |
|---|---|---|---|---|
| 11,626,001 | B1* | 4/2023 | Khmelev | G08B 21/10 340/532 |
| 2006/0282175 | A1* | 12/2006 | Haines | A61F 2/80 623/24 |
| 2007/0182367 | A1* | 8/2007 | Partovi | H02J 50/12 320/108 |
| 2007/0191965 | A1* | 8/2007 | Colvin | A61F 2/80 623/24 |
| 2009/0218884 | A1* | 9/2009 | Soar | H02J 50/10 320/108 |
| 2010/0131113 | A1* | 5/2010 | Even-Zohar | A61F 2/70 700/279 |
| 2011/0018498 | A1* | 1/2011 | Soar | H01F 27/36 320/108 |
| 2012/0133234 | A1* | 5/2012 | Da Costa Balas Ferreira | H02K 21/26 310/179 |
| 2012/0226197 | A1* | 9/2012 | Sanders | G06Q 10/087 600/587 |
| 2013/0317627 | A1* | 11/2013 | Loverich | H02K 7/1853 290/1 A |
| 2013/0321168 | A1* | 12/2013 | Mahony | A61B 5/318 340/870.07 |
| 2013/0324041 | A1* | 12/2013 | Pagani | H02J 50/70 455/41.1 |
| 2014/0288464 | A1* | 9/2014 | Stein | A61F 2/4657 600/595 |
| 2015/0066155 | A1* | 3/2015 | Haque | H02J 50/12 623/24 |
| 2015/0326044 | A1* | 11/2015 | Ashley | H02J 7/342 320/103 |
| 2015/0366504 | A1* | 12/2015 | Connor | A61B 5/6804 600/301 |
| 2015/0370320 | A1* | 12/2015 | Connor | A61B 5/1121 345/173 |
| 2016/0071397 | A1* | 3/2016 | Logan | G07C 9/00 340/687 |
| 2016/0134153 | A1* | 5/2016 | Miller | H02J 7/0042 320/103 |
| 2016/0242646 | A1* | 8/2016 | Obma | A61B 5/01 |
| 2016/0245665 | A1* | 8/2016 | Logan | G06K 19/027 |
| 2016/0317383 | A1* | 11/2016 | Stanfield | A61H 3/061 |
| 2017/0325525 | A1* | 11/2017 | Hyde | A61G 7/1051 |
| 2018/0001184 | A1* | 1/2018 | Tran | G16H 50/20 |
| 2018/0307314 | A1* | 10/2018 | Connor | G06F 3/017 |
| 2020/0119619 | A1* | 4/2020 | Krupenkin | H02J 7/32 |
| 2020/0341543 | A1* | 10/2020 | Thoresen | G06F 3/011 |
| 2020/0383395 | A1* | 12/2020 | Bean | H01M 10/44 |
| 2021/0196975 | A1* | 7/2021 | De Taboada | A61B 5/6804 |
| 2021/0344206 | A1* | 11/2021 | Danti | A45C 3/06 |
| 2023/0293104 | A1* | 9/2023 | Gross | A61F 2/38 623/20.32 |
| 2023/0338169 | A1* | 10/2023 | Rodgers | A61F 2/66 |

* cited by examiner

SMART GEAR

CROSS REFERENCE RELATED TO APPLICATIONS

This application claims priority from and the benefit of U.S. Provisional Application Ser. No. 62/983,308, entitled "SMART GEAR," filed Feb. 28, 2020. This U.S. Provisional Application is hereby incorporated by reference in its entirety for all purposes.

BACKGROUND

The present disclosure relates generally to smart gear or textile based wearable technologies. More particularly, the present disclosure relates to systems and methods for monitoring health conditions, powering electronic devices, and authenticating payments via smart gear.

This section is intended to introduce the reader to various aspects of art that may be related to various aspects of the present disclosure, which are described and/or claimed below. This discussion is believed to help provide the reader with background information to facilitate a better understanding of the various aspects of the present disclosure. Accordingly, it is understood that these statements are to be read in this light, and not as admissions of prior art.

Wearable devices may be used to monitor health conditions and patterns (e.g., heart murmurs, sleeping patterns, breathing activity). In particular, it is now recognized that smart gear that integrates fabric or textiles with electronic elements may be desirable. Smart gear may improve efficiency and provide convenience in retrieving data associated with health conditions and patterns. Furthermore, smart gear may allow noninvasive and continuous health monitoring as well as efficient power generation.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a system includes a fabric that may include one or more electrically conductive fibers, one or more sensors, or both. The one or more electrically conductive fibers, one or more sensors, or both are configured to transmit a signal. The system also includes one or more processors and one or more memory devices configured to store machine-readable instructions that, when executed by the one or more processors, cause the one or more processors to initiate a command based on the signal.

In a further embodiment, a garment incudes one or more electrically conductive fibers, one or more sensors, or both configured to transmit a signal. The one or more electrically conductive fibers may include one or more metal strands woven into the fabric. Further, the one or more sensors are coupled to the electrically conductive fibers.

In an additional embodiment, a smart gear system may include a fabric that includes one or more electrically conductive fibers, one or more sensors, or both. Additionally, the smart gear system may include transceiver circuitry that is external to the fabric and communicatively coupled to the one or more sensors, such that the transceiver circuitry is configured to transmit a signal.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
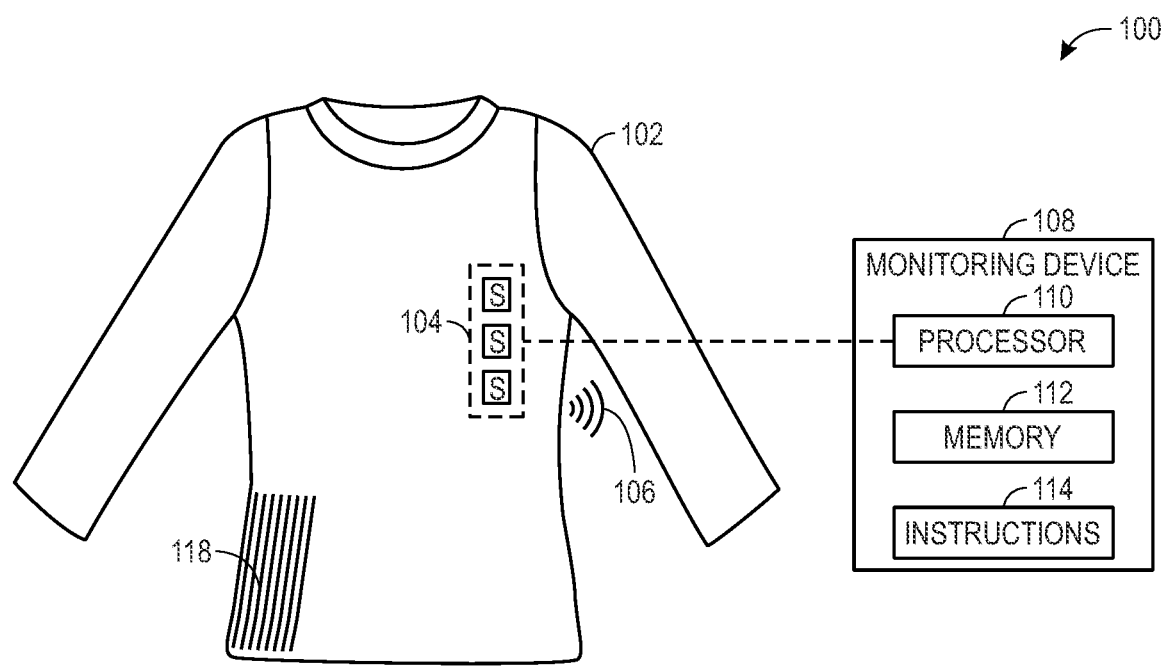
FIG. 1 illustrates a schematic diagram of monitoring health conditions via smart gear, in accordance with an embodiment of the present disclosure.

One or more specific embodiments of the present disclosure are described above. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As discussed in greater detail below, the present embodiments described herein improve efficiencies in monitoring health conditions, powering electronic devices, and authorizing payments via smart gear. Non-limiting examples of smart gear may include one or more sensors attached to non-conductive fabric, the one or more sensors embedded or woven in non-conductive fabric, and the one or more sensors integrated with electrically conductive fibers. As used herein, non-conductive fabric may be fabric that is not capable to conduct heat, electricity, or sound. A system that integrates technologies with fabrics for apparel, interior design, and other applications may be desirable, particularly in the fields of safety, medicine, sports, and security.

In one embodiment, smart gear may be used to monitor health patterns (e.g., sleeping patterns, smoking patterns, and body mass index patterns) and identify health conditions (e.g., heart murmurs, diabetes, and sleep apnea). By integrating electronic elements with textiles or fabrics, smart gear may improve efficiency and provide convenience in retrieving data associated with health conditions and patterns. Furthermore, smart gear may allow noninvasive and continuous health monitoring. In one example, smart gear may entail one or more sensors (e.g., blood glucose sensors, piezoelectric sensors, temperature sensors, heart rate sensors, micro-electromechanical sensors (MEMS), biochemical sensors, and biometric sensors) attached to non-conductive fabrics (e.g., clothing, shoes, and bedding). These one or more sensors may be woven or embedded into fabrics using flexible electronic techniques. Flexible electronics may be defined as electronic devices mounted on flexible plastic substrates such as polymide, polyether ether ketone (PEEK), or transparent, conductive polyester. Furthermore, the fibers of fabric or textiles used to manufacture the smart gear may, itself, be electrically conductive. Electronics (e.g., the one or more sensors, circuitry) may be directly integrated into the fabric by manufacturing the fabric using graphene fibers, optic fibers, or photoluminous fibers.

With the preceding in mind, FIG. 1 depicts a smart gear system 100 associated with monitoring health conditions and patterns via smart gear, according to implementations of the present disclosure. As shown in FIG. 1, an individual may own or otherwise be associated with a smart gear 102. Non-limiting examples of the smart gear 102 may include clothing (e.g., shirts, pants, and dresses), accessories (e.g., belts and watches), shoes, bedding, and other fabrics that are electrically conductive or include one or more electrical components. The smart gear 102 may include one or more sensors 104. In some embodiments, the one or more sensors 104 may be integrated (e.g., woven or embedded) into non-conductive fabrics. In other embodiments the smart gear 102 may include electrically conductive fibers, and the one or more sensors 104 may be integrated with electrically conductive fibers. Non-limiting examples of the one or more sensors 104 include blood glucose sensors, piezoelectric sensors, temperature sensors, heart rate sensors, micro-electromechanical sensors (MEMS), biochemical sensors, and biometric sensors.

In one embodiment, the one or more sensors 104 may be coupled to non-conductive fabrics via bands (e.g., armbands, waistbands), straps, clip-ons, and so forth. For example, an armband that includes circuitry, the one or more sensors 104, and other electronic components may be attached to an upper portion of a shirt sleeve near armpit region to measure body temperature. In another embodiment, the one or more sensors 104 may be embedded into the smart gear 102 by weaving or knitting techniques. The smart gear 102 may include but not limited to fabrics or textiles made out of materials such as polyester, nylon, cotton. In some embodiments, flexible electronics may be used in combination with weaving or knitting techniques in order to embed the one or more sensors 104 into the smart gear 102. Flexible electronics may enable electronic devices (e.g., circuitry, the one or more sensors 104) to be mounted on flexible plastic substrates such as polymide, polyether ether ketone (PEEK), or transparent, conductive polyester. In a further embodiment, the one or more sensors 104 may be integrated with electrically conductive fibers 118 of the smart gear 102. For example, electrically conductive fibers 118 may include optic or photoluminous fibers that may react to light, sound, and heat triggers. In some embodiments, non-conductive fibers of fabrics or textiles (e.g., nylon, polyester) associated with the smart gear 102 may be coated with graphene or other materials to produce the electrically conductive fibers 118. In other embodiments, the non-conductive fibers of fabrics associated with the smart gear 102 may be deposited with metal nanoparticles to enhance the electrical conductivity of the smart gear 102.

The smart gear 102 may enable monitoring of one or more health parameters via the one or more sensors 104. Non-limiting examples of the one or more health parameters include sleeping patterns, smoking patterns, body mass index patterns heart murmurs, diabetes, and sleep apnea. In particular, the one or more sensors 104 may include electrocardiogram (EKG) sensors, heart rate sensors, and pressure sensors to measure heart rate and detect heart murmurs or any other heart conditions to acquire the one or more health parameters. The one or more sensors 104 may also capture sleeping patterns (e.g., whether an individual sleeps on the side, back, and so forth) based on pressure sensors and sleeping disorders (e.g., sleep apnea) based on breathing activity monitored by various MEMS piezoelectric sensors that measure changes in pressure, acceleration, temperature, strain, and force by converting the changes to electrical charges. The movement and stretching of fabric, which may induce changes in pressure, strain, force, and so forth, may correlate to breathing activity. Breathing activity or data may also be used to monitor smoking habits. The one or more sensors 104 may include ultrasonic and strain gauge sensors to measure body mass index. In an additional example, diabetes may be detected by measure of ketone levels of the skin. Because ketone levels may serve as a surrogate for glucose levels, and ketones may be released by human skin, the one or more sensors 104 may include biochemical sensors that are capable of measuring ketone levels of fabrics or textiles that are in contact with the human skin.

As mentioned above, the one or more sensors 104 may be coupled to non-conductive fabric of the smart gear 102, woven or embedded in a non-conductive fabric of the smart gear 102, integrated with electrically conductive fibers of the smart gear 102, and so forth. After acquired health data is obtained as described above, the one or more sensors 104 may transmit a signal to an electronic display to display the health data. For example, a monitoring device 108 may include the electronic display.

The monitoring device 108 may include any suitable type of computing device. In some instances, the monitoring device 108 is a portable computing device such as a smartphone, tablet computer, wearable device, an electronic book reader, implanted computer, automotive computer, portable gaming platform, and so forth, the location of which may change throughout the course of a day or other period of time as one or more individuals move about. In some embodiments, the monitoring device 108 may also be a less portable type of computing device, such as a desktop computer, laptop computer, game console, smart appliance, and so forth.

The monitoring device 108 may include a processor(s) 110 (e.g., a microprocessor(s)) that may execute software programs to control the smart gear 102. Moreover, the processor 108 may include multiple microprocessors, one or more "general-purpose" microprocessors, one or more special-purpose microprocessors, and/or one or more application specific integrated circuits (ASICS), or some combination thereof. For example, the processor 110 may include one or more reduced instruction set (RISC) processors. The monitoring device 108 may include a memory device 50 that may store information such as control software, look up tables, configuration data, etc.

The memory device 112 may include a tangible, non-transitory, machine-readable medium, such as a volatile memory (e.g., a random access memory (RAM)) and/or a nonvolatile memory (e.g., a read-only memory (ROM), flash memory, a hard drive, or any other suitable optical, magnetic, or solid-state storage medium, or a combination thereof). The memory device 112 may store a variety of information, which may be suitable for various purposes. For example, the memory device 112 may store machine-readable and/or processor-executable instructions 114 (e.g., firmware or software) for the processor execution.

As mentioned above, the one or more sensors 104 or the electrically conductive fibers 118 may capture relevant health data and send it to a monitoring computing device 108 via a communication interface 106. In some embodiments, the communication interface 106 may involve wireless, low power communication protocols such as near-field communication (NFC) or radio-frequency identification (RFID) to transfer health data from the smart gear 102 to the monitoring computing device 108. In particular, the one or more sensors 104 or the electrically conductive fibers may include RFID tags or NFC labels to enable communication with the monitoring computing device 108.

Furthermore, the smart gear 102 and the monitoring computing device 118 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LAN (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

As may be appreciated, using the techniques provided herein, the smart gear 102 may monitor and identify health conditions and patterns. It may be desirable to maintain a history or record of health data over a suitable period of time (e.g., weekly, monthly, and yearly) For example, life insurance coverages may depend on the risk associated with the health data. The health data may include whether the applicant is a smoker, blood work performed on the applicant, previous illnesses acquired by the individual, and so forth. Thus, based upon the periods of time where high risk is identified with the health data, insurance coverage may cease or elevated coverages may be applied. In the case of elevated coverage, additional charges for the elevated coverage may be charged to an individual, specifically based on the periods where elevated coverage was identified as needed (e.g., when the individual was smoking). When low risk is associated with the health data is identified (e.g., normal bloods reports of the individual), coverage with minimized premiums may be observed by the individual.

In a further embodiment, smart gear may be used to power electronic devices such as mobile phones, laptops, and so forth. Physiological (e.g., breathing) and voluntary (e.g., stretching arms or legs) movement of a human body, may be used to power fabric associated with a wireless pocket of the smart gear, and in turn electronic devices. Smart gear may consist of one or more sensors integrated with electrically conductive fibers. The one or more sensors may by piezoelectric sensors that may convert mechanical energy into electrical energy. For example, breathing or stretching may apply pressure on the fabric or cause the fabric to move, which induces a change in pressure, acceleration, temperature, strain, or force. Such changes in mechanical energy may be converted to an electrical charge via the piezoelectric sensors. Thus, the electric charge may be used to power the fabric associated with the wireless pocket of the smart gear. By placing an electronic device into the wireless pocket, the electronic device may be charged via inductive charging or wireless charging. The wireless pocket may be any suitable size or shape. In some instance, the wireless pocket may be a part of shirts, jeans, jackets, and so forth. In some embodiments, the wireless pocket may be a wireless regions or patch of fabric. For example, the smart gear may include bedding, and the bedding may include a wireless region or patch used for powering electronic devices such as laptops, mobile devices, tablets, and so forth. In one embodiment, the wireless pocket may be removable from the smart gear to allow for washing of the smart gear to prevent damage or interfering with the charging function of the wireless pocket.

Figure 2:
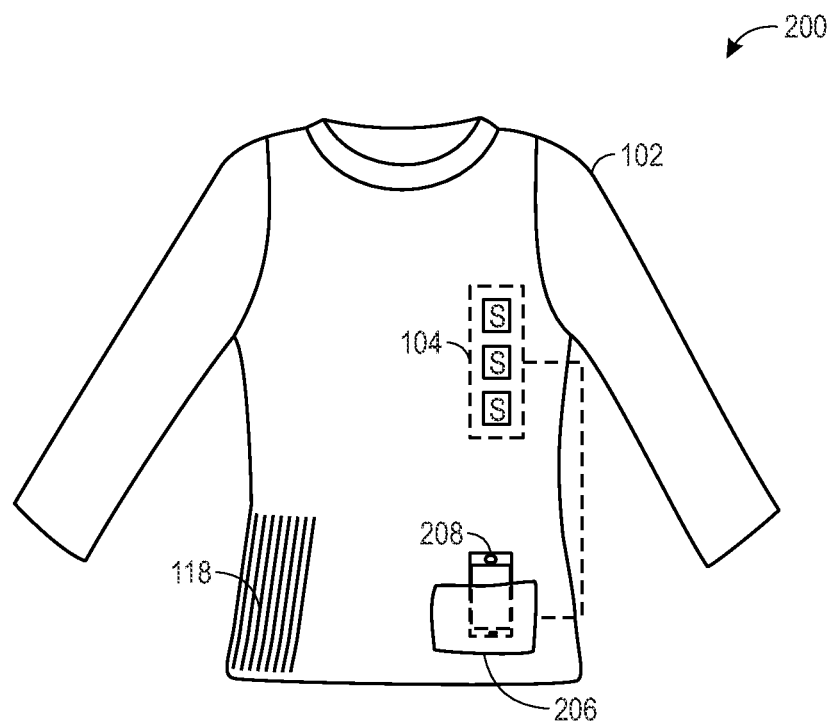
FIG. 2 illustrates a schematic diagram of powering electronic devices via smart gear, in accordance with an embodiment of the present disclosure.

With the preceding in mind, FIG. 2, illustrates smart gear system 200 of powering electronic devices via the smart gear 102. As mentioned above, the smart gear 102 may include clothing (e.g., shirts, pants, and dresses), accessories (e.g., belts and watches), shoes, bedding, and other fabrics that are electrically conducive and/or include one or more electrical components such as the one or more sensors 104. In some embodiments, the one or more sensors 104 may by piezoelectric sensors that convert mechanical energy into electrical energy. For example, breathing or stretching may apply pressure to the smart gear 102 or cause the fabric of the smart gear 102 to move, which induces a change in pressure, acceleration, temperature, strain, or force. Such changes in mechanical energy may be converted to an electrical charge via the piezoelectric sensors In additional and/or alternative embodiments, one or more sensors 104 may be integrated with the electrically conductive fibers 118. The electrically conductive fibers 118 may include optic or photoluminous fibers that may react to light, sound, and heat triggers. In some embodiments, fabrics or textiles of the smart gear 102 may include non-conductive fibers (e.g., nylon, polyester) coated with metal (e.g., graphene) or other materials that are electrically conductive. The combination of non-conductive fibers with materials that are electrically conductive may have similar electrical properties as the electrically conductive fibers 118. In other embodiments, the non-conductive fibers of the smart gear 102 may be deposited with metal nanoparticles to enhance the electrical conductivity of the smart gear 102.

In some embodiments, the one or more sensors 104 may be able to detect orientation of fibers of the smart gear 102. Based on the orientation of the fibers of the smart gear 102, the one or more sensors 104 may detect a body shape of the individual wearing the smart gear 102 (e.g., shirt with electrically conductive fibers). For example, fibers that are in an expanded state and/or adjusted orientation causing smart gear 102 curvature near the stomach region may indicate an individual with a protruding belly.

Further, the wireless pocket 206 may be formed using the electrically conductive fibers 118. The smart gear 102 may include any number of wireless pocket 206, which may be any suitable size or shape. In some instance, the wireless pocket 206 may be a part of shirts, jeans, jackets, and so forth. In some embodiments, the wireless pocket 206 may be a wireless region or a patch of fabric. For example, the smart gear 102 may include bedding, and the bedding may include a wireless region or patch used for powering electronic devices 208 such as laptops, mobile devices, tablets, and so forth. In one embodiment, the wireless pocket 206 may be removable from the smart gear 102 to allow for washing of the smart gear 102 without damaging or interfering with the inductive charging capabilities of the wireless pocket 206.

The electrical charge produced from the piezoelectric sensors based on movements from breathing and stretching may power the wireless pocket 206. In turn, the wireless pocket 206 may enable the powering of the electronic devices 208 via inductive or wireless charging. As used herein, inductive or wireless charging is a type of wireless power transfer based on electromagnetic induction. Further, communication between the one or more sensors 104, the electrically conductive fibers 118, and the wireless pocket 206 may be enabled by wireless near-field communication (NFC) or radio-frequency identification (RFID). For example, the one or more sensors 104 or the electrically conductive fibers 118 may include RFID tags or NFC labels to enable communication with the monitoring computing device 108.

Furthermore, the smart gear 102 and the wireless pocket 206 may communicate with one another, or with other computing devices, using one or more networks. Such networks may be similar to those described in FIG. 1. Similar to the smart gear 102 being used to generate power, prosthetics may also be used to generate electrical charge, as further discussed below.

In an additional embodiment, smart gear may be used to authorize payments. Smart gear (e.g., clothing, bedding that is electrically conductive), may include one or more electronic chips and sensors integrated with electrically conductive fibers. The one or more sensors may include fingerprint sensors that allows for secure storage of an individual's biometric data. The one or more electronic chips may include wireless near-field communication (NFC) or radio-frequency identification (RFID) to enable NCF or RFID low-power, wireless communication protocols. Payments may be authorized between two individuals by touching a portion (e.g., sleeve of a shirt) of an individual's smart gear to a portion of another individual's smart gear. This form of actuation for payment may be enabled by RFID of NFC communication.

Figure 3:
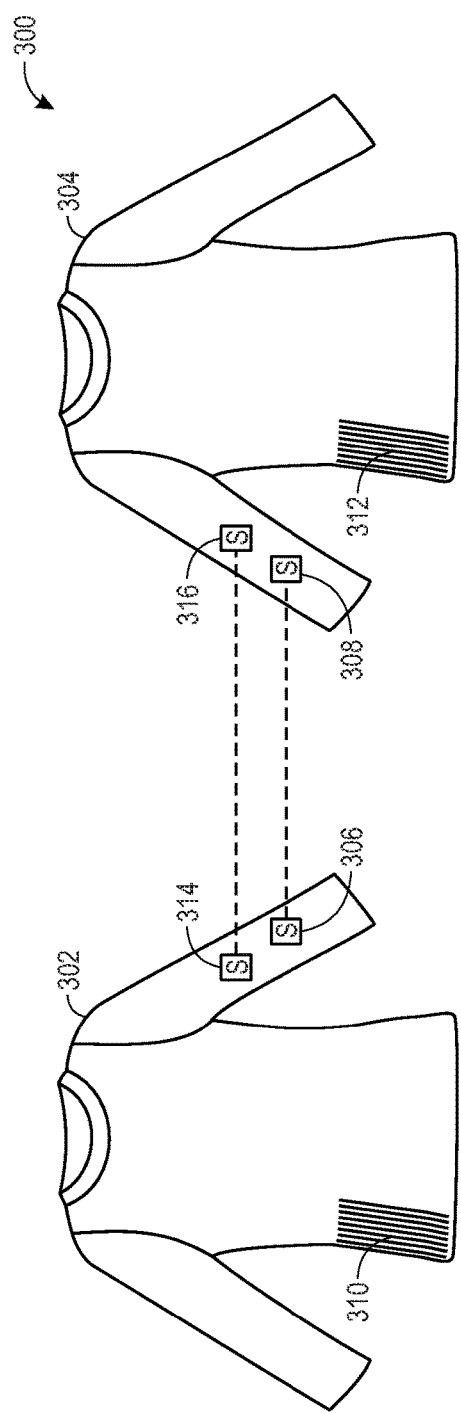
FIG. 3 illustrates a schematic diagram of authenticating payments via smart gear, in accordance with an embodiment of the present disclosure.

In turn, FIG. 3 illustrates system 300 of authenticating payments between a first individual who owns or is associated with smart gear 302 and a second individual who owns or is associated with smart gear 306. Both the smart gears 302 and 306 may include clothing (e.g., shirts, pants, and dresses), accessories (e.g., belts and watches), shoes, bedding, and textiles associated with interior design. The one or more sensors 304 and 308 of respective smart gears 302 and 306, may be integrated with their respective electrically conductive fibers 310 and 312. The electrically conductive fibers 310 and 312 may include optic or photoluminous fibers that may react to light, sound, and heat triggers. In some embodiments, non-conductive fibers of fabrics or textiles (e.g., nylon, polyester) associated with the smart gear 102 may be coated with graphene or other materials to produce the electrically conductive fibers 310 and 312. In other embodiments, the non-conductive fibers of fabrics associated with the smart gear 102 may be deposited with metal nanoparticles to enhance the electrical conductivity of the smart gear 102.

As discussed above, the one or more sensors 304 and 308 may include fingerprint sensors that allows for secure storage of an individual's biometric data. The one or more sensors 304 and 308 may be integrated with their respective electrically conductive fibers 310 and 312. After an individual has performed an identity authentication process via the fingerprint sensor, he or she may be authorized to use his or her smart gear for financial transactions or payments. Payments may be conducted via NFC or RFID communication. As a result, the electrically conductive fibers 310 and 312 may be integrated with their one or more electronic chips 314 and 316.

In particular, the smart gear 302 and the smart gear 304 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

Payments may be authorized or conducted between two individuals by touching a portion of an individual's smart gear to a portion of another individual's smart gear. For example, the first individual may touch the second individual's shirt sleeve, which is part of the second individual's (smart gear 302) with his or her shirt sleeve (smart gear 304). That is, a receiver and a transmitter external to the smart gear may be communicatively coupled to sensors of the smart gear. When the first individual touches the second individual's shirt sleeve, a receiver associated with the second individual's smart gear (e.g., shirt) receives, via its embedded sensors, an indication of a payment request from the first individual's smart gear. In response to the payment request, a transmitter associated with the second individual's smart gear (e.g., shirt) transmits a signal, via its embedded sensors, to authorize payment to the first individual's smart gear first individual's smart gear. In other embodiments, payments may be authorized or conducted between groups of individual, between a merchant and an individual, and so forth.

In some embodiments, the one or more sensors 306 and 208 and the one or more electronic chips 314 or 316 may be integrated with the electrically conductive fibers 310 and 312 as buttons, cuffs, and the like within the smart gear 302 and 304. The buttons, cuffs, and the like which contain the one or more sensors 306 and 208 and the one or more electronic chips 314 or 316 may be removable from the smart gear 302 and 304 to allow for washing of the smart gear 302 and 304.

Figure 4:
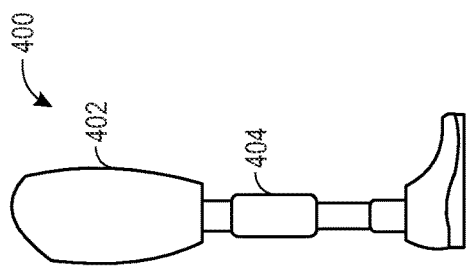
FIG. 4 illustrates a schematic diagram of generating power via prosthetics, in accordance with an embodiment of the present disclosure.

In a further embodiment, prosthetics (e.g., prosthetic leg, prosthetic knees) may be used to generate electrical charge or power. As such FIG. 4 illustrates system 400, in which prosthetics are used to generate power. System 400 may include a prosthetic limb 402 that has one or more internal shock absorbers 404. Non-limiting examples of the prosthetic limb 402 may include prosthetic legs, prosthetic knees, and prosthetic arms. The prosthetic limb 402 may generate power via absorption of kinetic energy by the one or more internal shock absorbers 404. For example, movement (e.g., running, walking) of the prosthetic limb 402 (e.g., prosthetic leg) may create kinetic energy. In some embodiments, the shock absorbers 404 may be spring-based shock absorbers or torsional-based shock absorber. The kinetic energy produced due to motion of the prosthetic limb 402 may be absorbed by the one or more internal shock absorbers 404 and converted into electrical energy. In turn in some embodiments, the electrical energy may be used to power internet of things (IOT) integrations of the prosthetic limb 402. Examples of the IOT integrations may include using power for local hotspots or for active screen covering of the prosthetic limb 402.

In additional and/or alternative embodiments, movement of a smart gear based on repetitive bending movements to provide electrochemomechanical and triboelectrical power generation. Triboelectrical power generation may result from the build-up of electrostatic charge due to motion of the smart gear via movement of a human body (e.g., bending, stretching).

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

While only certain features of the disclosure have been illustrated and described herein, many modifications and changes will occur to those skilled in the art. It is, therefore, to be understood that the appended claims are intended to cover all such modifications and changes as fall within the true spirit of the present disclosure. The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A system, comprising:
a fabric comprising one or more electrically conductive fibers, one or more sensors, or both, wherein the one or more electrically conductive fibers, the one or more sensors, or both are configured to transmit a signal;
one or more processors;
one or more memory devices configured to store machine-readable instructions that, when executed by the one or more processors, cause the one or more processors to initiate a command based on the signal; and
a prosthetic limb coupled to one or more internal shock absorbers wherein the internal shock absorbers are configured to provide power to one or more electrical components of the system coupled to the prosthetic limb based on motion of the prosthetic limb.

2. The system of claim 1, wherein the one or more electrically conductive fibers comprise one or more metal strands woven into the fabric.

3. The system of claim 1, wherein the one or more sensors comprise blood glucose sensors, heart rate sensors, temperature sensors, piezoelectric sensors, micro-electromechanical sensors (MEMS), biometric sensors, or any combination thereof.

4. The system of claim 1, wherein the one or more sensors are configured to acquire health data related to heart murmurs, sleep apnea, diabetes, body mass index patterns, breathing patterns, sleeping patterns, smoking patterns, or any combination thereof.

5. The system of claim 4, wherein the command comprises causing, by an electronic display, to display the health data.

6. The system of claim 1, wherein the fabric comprises one or more wireless charging regions comprising an inductive charger configured to power one or more electronic devices disposed in the one or more wireless charging regions via inductive charging.

7. The system of claim 6, wherein the signal comprises an energy signal, and wherein the one or more electrically conductive fibers, the one or more sensors, or both are configured to transmit the energy signal to the inductive charger of the one or more wireless charging regions.

8. The system of claim 6, wherein the command comprises authorizing a payment in response to receiving an indication of a payment request from a second fabric that is communicatively coupled to the fabric.

9. The system of claim 1, wherein the fabric comprises clothing, and wherein the one or more sensors are disposed in one or more buttons, one or more cuffs, or both of the clothing.

10. The system of claim 9, wherein the one or more buttons, the one or more cuffs, or both that comprise the one or more sensors are removable from the clothing.

11. The system of claim 1, wherein the one or more sensors are configured to detect a body shape based on an orientation of a plurality of fibers in the fabric.

12. A garment system, comprising:
a garment, comprising one or more electrically conductive fibers, one or more sensors, or both configured to transmit a signal, wherein the one or more electrically conductive fibers comprise one or more metal strands woven into fabric, and wherein the one or more sensors are coupled to the electrically conductive fibers;
one or more processors configured to initiate a command based on the signal; and
a prosthetic limb coupled to one or more internal shock absorbers, wherein the internal shock absorbers are configured to provide power to the one or more electrically conductive fibers, the one or more sensors or both.

13. The garment system of claim 12, wherein the one or more sensors are configured to communicatively couple to a transmitter and a receiver that are external to the garment.

14. The garment system of claim 13, wherein the receiver is configured to receive an indication of a payment request from a second garment via the one or more sensors.

15. The garment system of claim 14, wherein the transmitter is configured to transmit the signal to authorize payment to the second garment via the one or more sensors.

16. The garment system of claim 12, wherein the one or more sensors are configured to monitor heart murmurs, sleep apnea, diabetes, body mass index patterns, breathing patterns, sleeping patterns, smoking patterns, or any combination thereof.

17. The garment system of claim 13, comprising one or more wireless charging regions comprising an inductive charger configured to power one or more electronic devices, wherein the one or more wireless charging regions are removable from the garment.

18. A smart gear system, comprising:
a fabric comprising one or more electrically conductive fibers, one or more sensors, or both;
transceiver circuitry that is external to the fabric and communicatively coupled to the one or more sensors, wherein the transceiver circuitry is configured to transmit a signal;
one or more processors configured to initiate a command based on the signal; and
a prosthetic limb coupled to one or more internal shock absorbers, wherein the internal shock absorbers are configured to provide power to the electrically conductive fibers, the one or more sensors, the transceiver circuitry, or any combination thereof.

19. The smart gear system of claim 18, wherein the signal causes an electronic display to display health data acquired by the one or more sensors, authorize a payment, provide energy to an inductive charger of a wireless region of the fabric, or any combination thereof.

* * * * *